United States Patent [19]

Oppelt

[11] Patent Number: 4,766,888

[45] Date of Patent: Aug. 30, 1988

[54] SHOCK WAVE GENERATOR FOR AN APPARATUS FOR NON-CONTACTING DISINTEGRATION OF CALCULI IN THE BODY OF A LIFE FORM

[75] Inventor: Sylvester Oppelt, Bamberg, Fed. Rep. of Germany

[73] Assignee: Siemens Aktiengesellschaft, Berlin and Munich, Fed. Rep. of Germany

[21] Appl. No.: 70,936

[22] Filed: Jul. 8, 1987

[30] Foreign Application Priority Data

Jul. 14, 1986 [DE] Fed. Rep. of Germany ....... 3623775

[51] Int. Cl.[4] .............................................. A61B 17/22

[52] U.S. Cl. .................................. 128/24 A; 367/142; 367/175

[58] Field of Search ............... 367/140, 142, 174, 175; 128/328, 24 A, 804; 181/113, 118

[56] References Cited

U.S. PATENT DOCUMENTS 4,655,220 4/1987 Hahn et al. ......................... 128/328

4,669,472 6/1987 Eisenmenger ....................... 128/328

4,674,505 6/1987 Pauli et al. ......................... 128/328

4,697,588 10/1987 Reichenberger .................... 128/328

*Primary Examiner*—Ruth S. Smith

*Attorney, Agent, or Firm*—Hill, Van Santen, Steadman & Simpson

[57] ABSTRACT

A shock wave generator for an apparatus for non-contacting disintegration of calculi in the body of a life form has a membrane of electrically conductive material which terminates a volume filled with a shock wave conducting medium, and a coil having windings disposed adjacent the membrane. The coil is connectable to a high voltage source with two terminals. For maintaining a long useful life of the membrane without significantly reducing the efficiency of converting electrical energy into shock wave energy, the membrane is provided with a potential such that a positive difference in potential is present between one terminal of the coil and the membrane, and a negative difference in potential is present between the other terminal of the coil and the membrane.

4 Claims, 1 Drawing Sheet

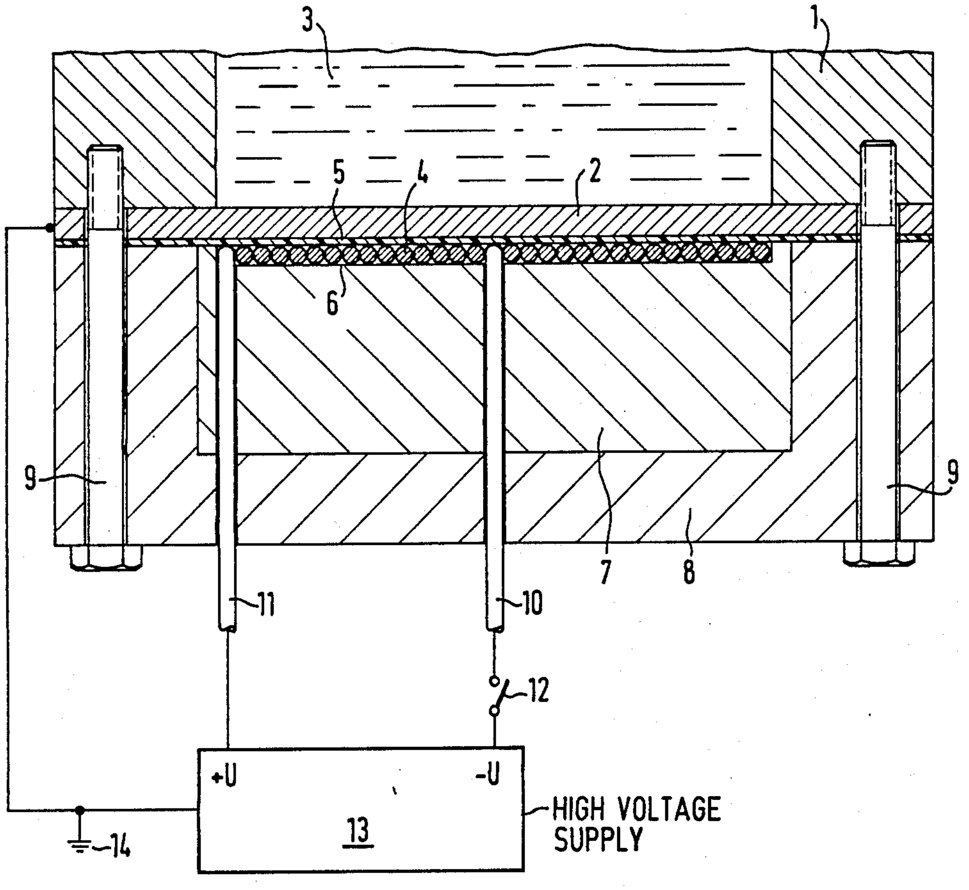
3
1
5
4
2
6
9
9
7
8
11
10
12
+U
-U
13
HIGH VOLTAGE SUPPLY
14

SHOCK WAVE GENERATOR FOR AN APPARATUS FOR NON-CONTACTING DISINTEGRATION OF CALCULI IN THE BODY OF A LIFE FORM

BACKGROUND OF THE INVENTION

1. Field of the Invention

The present invention is directed to a shock wave generator of the type suitable for use in an apparatus for non-contacting disintegration of calculi in the body of a life form, and in particular to such a shock wave generator having an electrically conductive membrane which is activated by a coil having windings disposed adjacent to the membrane.

2. Description of the Prior Art

A shock wave generator is disclosed in German OS No. 33 28 051 having, corresponding to U.S. Pat. No. 4,674,505, an electrically conductive membrane arranged parallel to a coil. Shock waves are generated by connecting the coil to a high voltage supply which has a capacitor charged to several kilovolts, for example 20 kV. The energy stored in the capacitor is suddenly discharged into the coil, so that the coil rapidly generates a magnetic field. Simultaneously, a current is generated in the membrane, the current being opposite to the current flowing in the coil. The current in the membrane thus generates an opposing magnetic field, causing the membrane to be suddenly moved away from the coil. The membrane terminates a volume which is filled with a shock wave conducting medium, such as fluid, by means of which the shock wave generated by the membrane movement is focussed to the calculi, for example, kidney stones, disposed in the body of a life form. Such focussing is accomplished with suitable means known to those skilled in the art, and causes disintegration of the calculi.

In order to achieve an optimal conversion of the electrical energy emitted by the high voltage supply into shock wave (impact) energy, conventional shock wave generators of the type described above require the membrane to be disposed as close as possible to the coil. Because of the difference in potential which necessarily exists between the coil and the membrane (which corresponds to the magnitude of the high voltage because the membrane is at ground in common with a terminal of the coil and a pole of the high voltage supply), the closeness of the membrane to the coil is limited because a minimum spacing must be observed in order to avoid voltage arcing between the membrane and the coil. Voltage arcing would deteriorate the effectiveness of the shock wave generator, and also leads to damage of the membrane, resulting in a shortened useful life thereof. In conventional shock wave generators, therefore, the distance between the coil and the membrane must be selected as a compromise in view of maintaining an adequate useful life of the membrane such that an unsatisfactory efficiency in the conversion of electrical energy into impact energy results.

SUMMARY OF THE INVENTION

It is an object of the present invention to provide a shock wave generator of the type described above wherein the membrane exhibits a high useful life without any significant reduction in the efficiency of the energy conversion.

The above object is achieved in accordance with the principles of the present invention in a shock wave generator wherein the membrane is provided with a potential such that a positive difference in potential exists between one terminal of the coil and the membrane, and a negative difference in potential exits between the other terminal of the coil and the membrane. In such a shock wave generator, the maximum difference in potential which can occur between the windings of the coil and the membrane is lower than the total amount of the high voltage supplied by the high voltage supply. Consequently, the coil can be disposed closer to the membrane without the risk of voltage arcing between the membrane and the coil, so that the shock wave generator, given the same electrical strength, exhibits a higher efficiency in the conversion of electrical energy into impact energy than known shock wave generators.

Optimum conditions exist if the coil is disposed relative to the membrane such that the magnitude of differences in potential existing between the individual windings of the coil and the membrane does not at any location exceed the magnitude of the greater difference in potential existing between the terminals of the coil and the membrane. It is thus assumed that the voltage drops at the terminals of the coil are negligible, i.e., the differences in potential existing between the windings of the coil immediately adjacent to the terminal and the membrane substantially correspond to the differences in potential between the terminals themselves and the membrane.

If the coil is arranged in a plane extending parallel to the membrane (the membrane also being planar), it is preferable that the differences in potential existing between the membrane and the terminals of the coil are respectively identical in magnitude, because the maximum difference in potential which can then occur between the membrane and the coil corresponds to only half of the amount of the total high voltage supplied by the high voltage supply.

In a further embodiment of the invention, the membrane is at ground potential. This assures that no high voltage will be applied to the shock wave conducting medium disposed in the volume of the housing, which medium may potentially come into contact under certain conditions with the life form, or with operating personnel.

Aside from the advantage of improved electrical strength, the shock wave generator constructed in accordance with the principles of the present invention, in comparison to conventional shock wave generators, allows a greater amount of electrical energy to be converted into impact energy, or alternatively, given the same electrical energy, a shock wave of shorter rise time to be generated, because the capacitor in the high voltage supply in the shock wave generator constructed in accordance with the principles of the present invention can be charged to a charging voltage which is higher in comparison to conventional shock wave generators. Thus the capacitor can either supply a greater energy output, increasing the square of the charging voltage, or given the same available energy, the capacitance thereof can be reduced. Reducing the capacitance of the capacitor in the high voltage supply has the advantage that the resonant circuit formed by the coil and the capacitor has a higher natural frequency, resulting in a shorter rise time of the current flowing through the coil, and thus in a shorter rise time of the shock wave.

This is of significant advantage when disintegrating calculi.

DESCRIPTION OF THE DRAWINGS

The single FIGURE is a side sectional view of a portion of a shock wave generator constructed in accordance with the principles of the present invention.

DESCRIPTION OF THE PREFERRED EMBODIMENTS

A shock wave generator constructed in accordance with the principles of the present invention has a housing 1 which has a volume 3 filled with a shock wave conducting medium, such as a fluid. The volume 3 is terminated by a membrane 2 consisting of electrically conductive material. A coil 4 having helically arranged windings is disposed opposite the membrane 2. An insulating foil 5 is disposed between the membrane 2 and the coil 4. The windings of the coil 4 are arranged on a seating surface 6 of an insulator 7, which is received in a cap or cover 8. The membrane 2, the insulating foil 5 and the cap 8 containing the insulator 7 with the coil 4 are secured to the housing 1 with bolts 9. For fixing the coil 4 to the seating surface 6 of the insulator 7, the space between the insulating foil 5 and the seating surface 6 of the insulator 7 is filled with an electrically insulating casting resin (not shown). Terminals 10 and 11 emerge to the exterior of the cover 8 through bores in the insulator 7 and the cover 8, by means of which the coil 4 is connectable through a switch means 12 to a high voltage supply 13. The high voltage supply 13 emits a current surge to the coil 4, causing the membrane 2 to be suddenly repelled from the coil 4, resulting in the formation of a shock wave in the medium within the volume 3. As a consequence of the high voltage across the coil 4, differences in potential occur between the membrane 2 and the individual windings of the coil 4.

The membrane 2 is at ground potential 14, whereas the terminal 11 is at a positive potential +U and the terminal 10 is at a negative potential −U. A positive difference in potential is thus present between the terminal 11 of the coil 4 and the membrane 2. By contrast, a negative difference in potential is present between the terminal 10 of the coil 4 and the membrane 2. The potentials +U and −U differ only in terms of the operational sign with respect to the ground potential 14, so that the two differences in potential are identical in magnitude.

The windings of the coil 4 in the shock wave generator shown in the drawing are disposed at a constant distance from the membrane 2, so that a difference in potential which at most corresponds to one-half of the magnitude of the high voltage emitted by the high voltage supply 13 occurs between the windings of the coil 4 and the membrane 2. In comparison to conventional shock wave generators, wherein the maximum difference in potential existing between the windings of the coil 4 and the membrane 2 would correspond to the entire magnitude of the high voltage, the coil 4 in the shock wave generator constructed in accordance with the principles of the present invention can be disposed closer to the membrane 2 without the risk of voltage arcing.

The exemplary embodiment shown in the drawing has a membrane 2 which is planar. It is also possible to construct a shock wave generator in accordance with the principles of the present invention, however, having a differently shaped membrane, such as a spherical membrane.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave generator comprising:

a high voltage supply having two supply terminals, one of said supply terminals being at a first potential and the other of said supply terminals being at a second potential lower than said first potential;

a housing having a volume filled with a shock wave conducting medium, said housing having an electrically conductive membrane terminating said volume on one side;

a coil having a plurality of windings disposed adjacent said membrane, and having two coil terminals with means for connecting said coil to said supply terminals of said high voltage supply so that one coil terminal is at said first potential and the other coil terminal is at said second potential; and means at a third potential between said first and second potentials connected to said membrane for applying said third potential to said membrane so that a positive difference in potential is present between said one coil terminal at said first potential and said membrane, and a negative difference in potential is present between said other coil terminal at said second potential and said membrane.

2. A shock wave generator as claimed in claim 1, wherein said means at a third potential is a means at a third potential for making said positive difference and said negative difference in potential equal in magnitude.

3. A shock wave generator as claimed in claim 1, wherein said membrane is planar.

4. A shock wave generator as claimed in claim 1, wherein said means at a third potential is a means at ground potential for applying said ground potential to said membrane.

* * * * *